United States Patent
Borsotti et al.

(10) Patent No.: US 12,049,682 B2
(45) Date of Patent: *Jul. 30, 2024

(54) PROCESS FOR OXIDATIVE CLEAVAGE OF VEGETABLE OILS CONTAINING MONOSATURATED FATTY ACID TRIGLYCERIDES

(71) Applicant: Novamont S.p.A., Novara (IT)

(72) Inventors: Giampietro Borsotti, Novara (IT); Francesca Digioia, Barengo (IT)

(73) Assignee: Novamont S.p.A., Novara (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/169,259

(22) Filed: Feb. 15, 2023

(65) Prior Publication Data

US 2023/0193420 A1    Jun. 22, 2023

Related U.S. Application Data

(60) Continuation of application No. 16/573,034, filed on Sep. 17, 2019, now Pat. No. 11,603,576, which is a division of application No. 15/542,852, filed as application No. PCT/EP2016/051067 on Jan. 20, 2016, now Pat. No. 10,450,631.

(30) Foreign Application Priority Data

Jan. 22, 2015  (IT) ................ MI2015A000060

(51) Int. Cl.
| | | |
|---|---|---|
| *B01J 47/02* | (2017.01) | |
| *B01J 39/04* | (2017.01) | |
| *B01J 39/05* | (2017.01) | |
| *B01J 39/20* | (2006.01) | |
| *C02F 1/26* | (2023.01) | |
| *C02F 1/42* | (2023.01) | |
| *C22B 3/00* | (2006.01) | |
| *C22B 3/42* | (2006.01) | |
| *C22B 34/36* | (2006.01) | |
| *C02F 101/20* | (2006.01) | |
| *C02F 101/32* | (2006.01) | |
| *C02F 103/32* | (2006.01) | |

(52) U.S. Cl.
CPC ............. *C22B 3/42* (2013.01); *B01J 39/04* (2013.01); *B01J 39/05* (2017.01); *B01J 39/20* (2013.01); *B01J 47/02* (2013.01); *C02F 1/26* (2013.01); *C02F 1/42* (2013.01); *C22B 23/0453* (2013.01); *C22B 34/36* (2013.01); *C22B 34/365* (2013.01); *C02F 2001/425* (2013.01); *C02F 2101/20* (2013.01); *C02F 2101/32* (2013.01); *C02F 2103/322* (2013.01); *Y02P 10/20* (2015.11)

(58) Field of Classification Search
CPC .... C22B 23/0456; C22B 34/365; B01J 36/05; B01J 39/04; B01J 47/02
See application file for complete search history.

(56) References Cited

U.S. PATENT DOCUMENTS

| | | |
|---|---|---|
| 4,675,108 A | 6/1987 | Dickerson et al. |
| 5,154,757 A | 10/1992 | Miller et al. |

FOREIGN PATENT DOCUMENTS

| | | |
|---|---|---|
| EP | 0 666 108 A1 | 1/1995 |
| WO | WO-2007/039481 A1 | 4/2007 |
| WO | WO-2008/138892 A1 | 11/2008 |
| WO | WO-2011/080296 A1 | 7/2011 |

OTHER PUBLICATIONS

Junji Shibata et al., "Recovery to tungsten and cobalt from tungsten carbide tool waste by hydrometallurgical method", Geosystem Engineering, (2014) 17:2, 120-124.

*Primary Examiner* — Zulmariam Mendez
(74) *Attorney, Agent, or Firm* — POLSINELLI PC

(57) ABSTRACT

This invention relates to a process for the recovery of cobalt ions and tungstic acid and/or its derivatives from aqueous solutions, such as in particular the spent catalytic waters deriving from processes for the oxidative cleavage of vegetable oils. In particular this invention relates to a process for the recovery of cobalt ions and tungstic acid and/or its derivatives which provides for the use of cation-exchange resins.

20 Claims, No Drawings

PROCESS FOR OXIDATIVE CLEAVAGE OF VEGETABLE OILS CONTAINING MONOSATURATED FATTY ACID TRIGLYCERIDES

CROSS REFERENCE TO RELATED APPLICATIONS

This application is a Continuation of U.S. application Ser. No. 16/573,034, filed on Sep. 17, 2019, now U.S. Pat. No. 11,603,576 B2, and which is a Divisional of U.S. application Ser. No. 15/542,852, filed on Jan. 20, 2016, which is the National Phase filing under 35 U.S.C. § 371 of PCT/EP2016/051067 filed on Jan. 20, 2016; which application in turn claims priority to Application No. MI2015A000060 filed in Italy on Jan. 22, 2015 under 35 U.S.C. § 119. The entire contents are hereby incorporated by reference.

DESCRIPTION

This invention relates to a process for recovering cobalt ions and tungstic acid and/or its derivatives from aqueous solutions, such as in particular the spent catalytic waters deriving from processes for the oxidative cleavage of vegetable oils. In particular this invention relates to a process for the recovery of cobalt ions and tungstic acid and/or its derivatives, which provides for the use of cation-exchange resins.

Vegetable oils are now an important raw material for the chemical industry on account of the ever more pressing need to identify raw materials of renewable origin which are alternatives to conventional petroleum sources.

For example WO 2008/138892 and WO 2011/80296 describe processes for oxidative cleavage, which, starting from vegetable oils containing monounsaturated fatty acid triglycerides, make it possible to produce intermediates for the preparation of polyesters, such as for example the saturated dicarboxylic acids, azelaic acid or brassylic acid. Typically the said processes provide for at least two immediately consecutive reaction stages: a first stage of hydroxylation of the double bond present in the monounsaturated fatty acid triglycerides to yield a vicinal diol and a subsequent second stage of oxidation of the two hydroxyl groups of the vicinal diol into carboxylic groups, obtaining a mixture comprising saturated monocarboxylic acids and saturated carboxylic acid triglycerides having more than one acid group.

These processes preferentially make use of different catalysts to increase the reaction rate and in general improve the yield and selectivity of the two reactions involved. For example catalysts such as tungstic acid and/or its derivatives, such as for example, phosphotungstic acid, are preferably used for the hydroxylation stage, while catalysts based on cobalt salts, such as for example cobalt acetate, cobalt chloride, cobalt sulfate, cobalt nitrate or cobalt bromide, are used for the oxidation stage. At the end of the hydroxylation stage, the catalyst is typically not separated from the reaction medium, and therefore mixes with the catalyst from the oxidation stage. Typically, at the end of the oxidative cleavage process the spent catalytic waters which are separated from the reaction products contain cobalt ions and tungstic acid and/or their derivatives, such as for example phosphotungstic acid, pertungstic acid and polytungstates, which may also be substituted with cobalt ions.

From the point of view of industrial production, the use of two different catalysts in two immediately consecutive stages of hydroxylation and oxidation therefore gives rise to the need to develop treatments to separate and recover the catalysts with a view to reusing them in the process so as to help reduce the costs of disposing of the catalytic waters, as well as the environmental impact of the processes themselves.

Starting from this technical problem, it has now been discovered that it is possible to effectively recover both cobalt ions and tungstic acids and/or their derivatives from an aqueous solution through a process comprising the following stages:

a) removing the cobalt ions by placing the said aqueous solution in contact with a cation-exchange resin;
b) separating the said aqueous solution from the cation-exchange resin;
c) concentrating the said aqueous solution obtained from stage b, obtaining a concentrated aqueous solution containing tungstic acid and/or its derivatives;
d) eluting cobalt ions from the cation-exchange resin in stage b, using an acid aqueous solution.

The process according to this invention is particularly suitable for recovering and effectively and economically separating cobalt ions and tungstic acid and/or its derivatives, such as in particular phosphotungstic acid, pertungstic acid and polytungstates, even when substituted with cobalt ions, from spent catalytic waters such as for example those originating from the processes of oxidative cleavage of vegetable oils such as those described in WO 2008/138892 and WO 2011/80296. The process can also be used for the recovery and separation of cobalt ions and tungstic acid and/or its derivatives which are also present in aqueous solutions of different origin. For simplicity of description reference will always be made to the spent catalytic waters in the rest of the description, this term also being intended to include any other aqueous solution having similar compositional characteristics without any distinction as to origin.

In stage a) of the process according to this invention the spent catalytic waters from which it is intended to recover the cobalt ions and tungstic acid and/or its derivatives are placed in contact with a cation-exchange resin which is capable of adsorbing the said cobalt ions. This stage may be performed in any equipment suitable for the purpose known to those skilled in the art, such as for example vessels, stirred reactors and tanks, mixers and ion-exchange columns. In order to maximise intimate contact between the cation-exchange resin and the waters containing cobalt ions and tungstic acid and/or its derivatives, said stage a) is advantageously performed in one or more ion-exchange columns, which may also be arranged in ranks or in sequence, depending upon the desired configuration for the process. For example, stage a) of the process according to this invention may be carried out using a single ion-exchange column or two or more ion-exchange columns placed in series. Depending upon the initial concentration of the waters containing the cobalt ions and the tungstic acid and/or its derivatives, those skilled in the art will be capable of selecting the most suitable configuration. Where not explicitly described otherwise, when reference is made in this invention to a treatment performed in an ion-exchange column this also means process configurations comprising two or more ion-exchange columns placed in series. Where the process according to this invention is carried out in continuous mode, stage a) may also be carried out using two or more cation-exchange resins, preferably two or more ion-exchange columns in parallel, which can work simultaneously or alternately, thus making it possible to regenerate the spent resins without interrupting the process.

As is known, cation-exchange resins and more generally ion-exchange resins comprise a polymer matrix (generally granules of a few millimetres in diameter) in which ions available for ion exchange are trapped or incorporated. In the process according to this invention crosslinked cation-exchange resins, more preferably of the strong acid type, in which the acid functional group preferably comprises sulfonic groups, are preferably used. Examples of cation-exchange resins of the strong acid type used in the process according to this invention are the resins: Amberlite™ IR100 Na. Amberlite™ IR-118(H), Amberlite™ IR-120 (plus), Amberlite™ IR-120) Na, Amberlite™ IR-122Na, Amberlite™ 252 Na, Amberlite™ SRIL Na Amberlyst™ XN-1010, Amberlyst™ 15WET, Amberlyst™ 36 WET, Amberjet™ 1200 Na, Amberjet™ 1000Na, Amberjet™ 1000(H), Amberjet™ 1300H, Amberjet™ 1300Na, Amberjet™ 4200 Cl, Amberjet™ 4600 Cl, Dowex® 50WX2-100, Dowex® 50WX2-200, Dowex® 50WX2-400, Dowex® 50WX4-50, Dowex® 50WX4-100, Dowex® 50WX4-200, Dowex® 50WX4-200R, Dowex® 50WX4-400, Dowex® 50WX8-100, Dowex® 50WX8-200, Dowex® 50WX8-400, Dowex® HCR-S, Dowex® HCR-W2, Dowex® 88, Dowex® 650C, Dowex Marathon™ C, Dowex Marathon™ MSC-1, Duolite™ C-26.

Preferably the cation-exchange resins in stage a) of the process according to this invention are characterised by a concentration of active sites which is greater than or equal to 1.8 and less than or equal to 4.8, preferably greater than or equal to 4.4 and less than or equal to 4.7 meq/gram (determined on the anhydrous resin).

When stage a) of the process according to this invention is carried out in an ion-exchange column, the spent catalytic waters are fed to the said stage, preferably at a flow rate of between 1 and 50, more preferably between 1 and 5, and even more preferably between 1 and 3 BV*/h (LHSV). Preferably stage a) of the process according to this invention is carried out at a temperature of ambient temperature (25 C) or above and may be carried out up to the maximum temperature at which the cation-exchange resin can be used. In a preferred embodiment stage a) of the process according to this invention is carried out at temperatures of 15 to 85° C., preferably between 25 and 80° C. In a preferred embodiment when the tungstic acid and/or its derivatives is a polytungstate, stage a) is preferably carried out at temperatures of 15-30° C., thus leading to particularly high yields of recovery of cobalt ions and polytungstates.

As far as the pH of the spent catalytic waters fed to stage a) of the process according to this invention is concerned, this preferably lies between 2.5 and 4, more preferably between 2.7 and 3.0.

Stage a) of the process according to this invention is more effective in terms of the adsorption of cobalt ions if, before they are placed in contact with the cation-exchange resin, the spent catalytic waters have been previously purified of any organic compounds which may be present. For example, when the catalytic waters which have to be fed to stage a) of the process according to this invention derive from processes of the oxidative cleavage of vegetable oils, these are separated from the process flow containing the organic phase with the reaction products of the said oxidative cleavage. Depending upon the quantity and the nature of any organic compounds which may be present, this preliminary purification is carried out using techniques for the purpose which are known to those skilled in the art, such as for example settling or liquid/liquid extraction.

In a preferred embodiment separation of the first organic phase from stage a) may be carried out by settling. In order to assist settling, an organic solvent, more preferably selected from the group comprising n-hexane, n-heptane, n-octane, n-nonanoic acid and mixtures thereof, even more preferably n-octane, n-nonanoic acid and mixtures thereof are preferably added. In a preferred embodiment the preliminary purification to obtain the catalytic waters which have to be fed to stage a) of the process is carried out by settling in the presence of 5-20% by volume, preferably 7-12% by volume, of organic solvent with respect to the total volume of the flow which has to be purified. When carried out in the presence of an organic solvent this settling is carried out at temperatures of ambient temperature (25° C.) or above, preferably at least 5° C. below the boiling point of the organic solvent or any azeotrope which the latter forms with water. When this settling is carried out using n-octane as organic solvent the temperature preferably lies between 60 and 90° C.

Depending upon the starting characteristics of the spent catalytic waters, one or more further pre-treatments selected from centrifuging, filtration, microfiltration, nanofiltration, ultrafiltration, osmosis or other suitable solid/liquid separation techniques and combinations thereof may be carried out before stage a) of the process according to this invention.

At the end of stage a) the cobalt ions originally present in the spent catalytic waters are preferably almost completely adsorbed onto the cation-exchange resin. In fact, the catalytic waters separated out from stage b) of this process have a cobalt ion content of less than 5 ppm, preferably less than 2 ppm. This cobalt ion concentration is in fact sufficiently low not to have a prejudicial effect on subsequent stages of the process and subsequent recovery of the tungstic acid and/or its derivatives. In stage b) of the process according to this invention the catalytic waters may be separated from the cation-exchange resin according to any method known to those skilled in the art for separating a solid phase, such as ion-exchange resin, from a liquid phase, for example by means of filtration, centrifuging, sedimentation, or using any combination of these methods. This separation may be performed in equipment other than that in which stage a) has been carried out, or in the same equipment. For example, when stage a) of the process is carried out in an ion-exchange column, separation of the catalytic waters from the cation-exchange resin typically takes place in the terminal part of the column, for example through a septum which retains the resin and allows the catalytic waters to flow out.

Depending upon the concentration of tungstic acid and/or its derivatives in the catalytic waters separated from the cationic resin, one or more treatments for concentrating the said catalytic waters in order to remove part of the water present are carried out in stage c) of the process according to this invention. This stage c) may be carried out using any method known to those skilled in the art, for example by one or more water evaporation treatments. Those skilled in the art are capable of identifying the desirable operating conditions, for example pressure and temperature, to remove the appropriate quantity of water.

Typically the aqueous solution obtained at the end of stage c) of this process has a concentration of tungstic acid and/or its derivatives, expressed as tungsten concentration, of between 10 and 15% by weight and a concentration of cobalt ions of less than 50 ppm. Surprisingly, it has been discovered that such an aqueous solution can be used for preparation of the catalytic solution for the hydroxylation stage in oxidative cleavage processes such as those described in WO 2008/138892 and WO 2011/80296, making it possible to obtain reaction yields, under the same reaction conditions, which are wholly comparable with those which can be achieved using fresh catalytic solutions of tungstic acid and/or its derivatives. This makes it possible to use the process according to this invention as a treatment for the recovery and regeneration of catalysts in such oxidative cleavage processes, thus helping to reduce the costs of the disposal of catalytic waters and the environmental impact of these processes.

The concentrated aqueous solution containing tungstic acid and/or its derivatives obtained at the end of stage c) of this process, may be further treated to recover tungstic acid and/or its derivatives. Such a recovery stage is advantageously carried out using one or more separation treatments, for example by distillation, liquid/liquid extraction, adsorption, precipitation, crystallisation or combinations thereof. Those skilled in the art are capable of selecting the appropriate method of recovery according to the concentration of the tungstic acid and/or derivatives present in the starting aqueous solution.

Preferably, the recovery stage of the process according to this invention is carried out by means of a treatment precipitating out the tungstic acid and/or its derivatives.

Precipitation of tungstic acid and/or its derivatives may be achieved, for example by progressively concentrating the acids by evaporating the water or reducing solubility, for example by lowering the pH or temperature of the aqueous solution. It is also possible to combine several methods of precipitation, for example by first concentrating the acids through the evaporation of water and subsequently reducing their solubility by reducing the temperature of the remaining aqueous solution.

The precipitate obtained can then be separated from the aqueous solution by means of any of the methods known to those skilled in the art, for example by filtering or centrifuging, or using any combination of these methods.

The tungstic acid and/or its derivatives separated out at the end of the recovery stage can subsequently be further purified. The said purification stage may be performed by means of one or more treatments selected from drying, lyophilisation, distillation, liquid/liquid extraction, adsorption or crystallisation.

In stage d) of the process according to this invention the cation-exchange resin separated from the catalytic waters at the end of the stage b) is placed in contact with an acid aqueous solution. This brings about elution of the adsorbed cobalt ion and at the same time regenerates the cation-exchange resin which can be reused in subsequent treatments according to stage a) of this process. Preferably the said acid aqueous solution is prepared from an acid preferably selected from the group comprising hydrochloric acid, sulfuric acid, phosphoric acid, hydrobromic acid, acetic acid, or even more preferably sulfuric acid.

Said stage d) may be performed in an item of equipment which is different from that in which stage a) is performed, or in the same equipment. For example when stage a) of the process is carried out in an ion-exchange column, elution of the cobalt ions from the cation-exchange resin is typically carried out in the same column, feeding acid aqueous solution to it.

Those skilled in the art will be capable of identifying suitable quantities of acid aqueous solution, its pH and contact time, in order to quantitatively elute cobalt ions from the cation-exchange resin. Acid aqueous solution characterised by a pH of less than 0.5 may preferably be used. In a preferred embodiment of this invention elution of cobalt ions from the cation-exchange resin is carried out by using up to 10 parts by weight per part of cation-exchange resin of an acid aqueous solution having a pH of less than 0.5.

In order to maximise the elution yield stage d) of the process according to this invention may be repeated more than once, each time feeding one or more aliquots of fresh acid aqueous solution, preferably with a progressively decreasing pH.

When stage a) is carried out in an ion-exchange column, the elution of cobalt ions may be further favoured by feeding the acid aqueous solution in countercurrent flow with respect to the flow of catalytic waters fed during stage a). This makes it possible to minimise the volume of acid aqueous solution required to elute the cobalt ions.

The aqueous solution obtained at the end of stage d) of this process may be used as such, or may be concentrated or diluted and may be further purified to remove the excess acid in order that it may subsequently be used to prepare the catalytic solution in the oxidation stage of catalytic cleavage processes, such as those described in WO 2008/138892 and WO 2011/80296, obtaining reaction yields which for the same reaction conditions are wholly comparable with those which can be obtained using fresh catalytic solutions containing cobalt.

The aqueous solution obtained at the end of stage d) of this process may also be further treated to recover the cobalt present therein. Such a recovery stage may advantageously be carried out using one or more separation treatments, for example by distillation, complexing, adsorption, precipitation, crystallisation, electrolysis or combinations thereof. Those skilled in the art will be in a position to select the appropriate means for recovery, depending upon the concentration of cobalt ions present in solution and the form in which they wish to recover the cobalt.

In a preferred embodiment of the process according to this invention, the recovery stage of the process according to this invention is carried out by means of treatment precipitating out the cobalt in the form of hydroxide which is subsequently filtered and redissolved in the presence of an acid, preferably selected from the group comprising hydrochloric acid, sulfuric acid, hydrobromic acid, phosphoric acid or acetic acid, more preferably acetic acid, thus re-obtaining a cobalt salt such as, for example cobalt acetate, cobalt chloride, cobalt sulfate, cobalt phosphate or cobalt bromide. In a preferred embodiment the cobalt recovery stage is carried out by precipitating out the cobalt as hydroxide, filtering the said hydroxide and redissolving it in acetic acid to obtain cobalt acetate.

It is also possible to achieve precipitation of the cobalt by adding a salt comprising a counter-ion capable of forming an insoluble salt with cobalt (precipitation by ion exchange) to the aqueous solution. It is also possible to combine several methods of precipitation, for example first concentrating the aqueous solution by evaporating the water and subsequently reducing the solubility of the salt by lowering the temperature of the remaining aqueous solution.

The precipitate obtained can then be separated from the aqueous solution by means of any of the methods known to those skilled in the art, for example by filtering or centrifuging, or using any combination of these methods.

The cobalt salt separated out at the end of the recovery stage may then be subsequently purified. The said purification stage may be carried out using one or more treatments selected from drying, lyophilisation, distillation, liquid/liquid extraction, or adsorption crystallisation. The invention will now be described through an Example which is intended to be for illustrative purposes and does not limit the invention.

EXAMPLE 1

28 kg of process flow originating from stage b) of a process for the oxidative cleavage of sunflower oil having a high oleic acid content carried out in accordance with Example 1 in application WO 2008/138892 were reheated to 80° C. in the presence of 2.8 kg of n-octane and allowed to settle until an organic phase had separated out, thus obtaining 8.4 litres of spent catalytic waters containing approximately 2400 ppm of cobalt ions and tungstic acid and/or its derivatives in a concentration corresponding to approximately 8000 ppm of tungsten.

Subsequently the spent catalytic waters obtained after separation of the organic phase were fed by gravity at 25° C. and BV/H=2 to an ion-exchange column (height 1 m and diameter 40 mm) packed with 216.2 grams (dry weight, corresponding to 800 ml of wet resin) of Amberlyst™ 15WET resin (concentration of active sites on the dry resin=4.7 eq/kg: concentration of active sites on the wet resin=1.8 meq/ml; surface area 53 m$^2$/g, pore diameter=300 Å).

During the treatment it was possible to establish that cobalt was effectively being adsorbed by the resin by observing progressive colouration of the resin bed. Table 1 shows details of the amount of adsorption (expressed as cm of colouration of the resin bed) as a function of the volume of the catalytic waters fed and the residual cobalt concentration in the aqueous solution obtained at the exit from the column, once separated from the cation-exchange resin.

TABLE 1

| Residual cobalt concentration in waters separated from the resin (ppm) | Cobalt adsorption (cm colouration of the resin bed) | Catalytic waters fed (ml) |
| --- | --- | --- |
| 0.15 | 25 | 1766 |
| 0.08 | 41 | 3561 |
| 0.06 | 60 | 5242 |
| 0.03 | 79 | 7256 |
| 0.16 | 86 | 7806 |
| 0.11 | 92 | 8216 |
| 0.06 | 93 | 8423 |

The aqueous solution separated from the cation-exchange resin was subsequently concentrated by evaporating off approximately 90% of the water, thus obtaining an aqueous solution containing tungstic acid and/or its derivatives in a concentration corresponding to approximately 80000 ppm of tungsten. The said solution was used as a catalytic solution in a reaction for the hydroxylation of vegetable oils, and revealed no differences of any kind with respect to a fresh solution having the same concentration.

6.3 kilograms of an aqueous solution of sulfuric acid (sulfuric acid concentration 6.5% by weight) were fed countercurrently to the ion-exchange column containing the cation-exchange resin on which the cobalt was adsorbed, separating out an aqueous solution containing approximately 3150 ppm of cobalt ions, indicating almost total recovery of the cobalt initially present in the spent catalytic waters.

EXAMPLE 2

Example 1 was repeated, feeding 8.6 litres of the same spent catalytic waters containing 2400 ppm of cobalt ions and tungstic acid and/or its derivatives in a concentration corresponding to approximately 8000 ppm of tungsten to the ion-exchange column containing the cation-exchange resin from which the cobalt had been eluted at the end of Example 1.

During the treatment it was possible to verify that cobalt was effectively being newly adsorbed from the resin through observing progressive colouration of the resin bed. In a similar way to Example 1, Table 2 shows details of the amount of adsorption (expressed as cm of colouration of the resin bed) as a function of the volume of the catalytic waters fed and the residual cobalt concentration in the aqueous solution obtained at the exit from the column, once separated from the cation-exchange resin.

TABLE 2

| Residual cobalt concentration in waters separated from the resin (ppm) | Cobalt adsorption (cm colouration of the resin bed) | Catalytic waters fed (ml) |
| --- | --- | --- |
| 0.32 | 13.5 | 863 |
| 0.55 | 32 | 2702 |
| 0.61 | 54 | 4854 |
| 0.72 | 76,5 | 6750 |
| 0.69 | 92 | 8667 |

The aqueous solution separated out from the cation-exchange resin was then subsequently concentrated by evaporating approximately 90% of the water, thus obtaining an aqueous solution containing tungstic acid and/or its derivatives in a concentration corresponding to approximately 80000 ppm of tungsten. The said solution was used as a catalytic solution in a reaction for the hydroxylation of vegetable oils without differences of any kind in comparison with a fresh solution at the same concentration.

2.1 kilograms of an aqueous solution of sulfuric acid (sulfuric acid concentration 6.5% by weight) were fed countercurrently to the ion-exchange column containing the cation-exchange resin on which the cobalt was adsorbed, separating out an aqueous solution containing 9830 ppm of cobalt ions, indicating almost total recovery of the cobalt initially present in the spent catalytic waters and maintaining the effectiveness of the cationic resin.

The invention claimed is:

1. A process for oxidative cleavage of vegetable oils containing monounsaturated fatty acid triglycerides comprising:
   1) a first step of hydroxylation of the double bond present in the monounsaturated fatty acid triglycerides in the presence of a catalyst comprising tungstic acid and/or its derivatives, to yield a vicinal diol,
   2) a subsequent second step of oxidation of the vicinal diol in the presence of catalysts comprising cobalt salts, thereby obtaining a mixture comprising saturated monocarboxylic acids and saturated carboxylic acid triglycerides having more than one acid group,
   3) a step of separation of an aqueous solution containing cobalt ions and tungstic acid and/or their derivatives from the mixture of step 2) and
   4) a step of separation of cobalt ions from said aqueous solution of step 3) comprising the operations of:
      a) removing the cobalt ions by placing the aqueous solution in contact with a cation-exchange resin,
      b) separating the aqueous solution from the cation-exchange resin;
      c) concentrating the aqueous solution obtained from stage b, thereby obtaining a concentrated aqueous solution containing tungstic acid and/or its derivatives, d) eluting cobalt ions from the cation-exchange resin in stage b, using an acid aqueous solution, thereby obtaining an aqueous solution comprising cobalt ions, wherein the aqueous solution obtained at the end of step 4-d) is used to prepare the catalyst for the oxidation step 2).

2. The process according to claim 1 wherein the tungstic acid derivatives of step 1) are selected from the group consisting of phosphotungstic acid, pertungstic acid and polytungstates and their cobalt salts.

3. The process according to claim 1 wherein the cobalt salts of step 2) are selected from the group consisting of cobalt acetate, cobalt chloride, cobalt sulfate, cobalt nitrate and cobalt bromide.

4. The process according to claim 1, wherein at the end of step 4-c) the concentration of tungstic acid and/or its derivatives in the concentrated aqueous solution, expressed as tungsten concentration, is of between 10 and 15% by weight and the concentration of cobalt ions is of less than 50 ppm.

5. The process according to claim 1, comprising before step 4-a) a preliminary purification step for separating an organic phase from the aqueous solution.

6. The process according to claim 5, in which the separation of the organic phase is performed by decantation.

7. The process according to claim 6, in which the decantation is performed in presence of an organic solvent.

8. The process according to claim 7, in which the organic solvent is selected from the group consisting of n-hexane, n-heptane, n-octane, n-nonanoic acid and mixtures thereof.

9. The process according to claim 8, in which the organic solvent is n-octane, nonanoic acid or mixtures thereof.

10. The process according to claim 1, in which the cationic exchange resin is crosslinked.

11. The process according to claim 1, in which the cation-exchange resin is of the strong acid type.

12. The process according to claim 11, in which the functional group of the cation-exchange resin of the strong acid type is constituted by sulphonic groups.

13. The process according to claim 1, in which the step 4-a) is performed with an ionic exchange column.

14. The process according to claim 13, in which the aqueous solution is fed to step a) with a flow rate comprised between 1 and 50 BV*/h (LHSV).

15. The process according to claim 2, in which the step 4-a) is performed with an ionic exchange column.

16. The process according to claim 3, in which the step 4-a) is performed with an ionic exchange column.

17. The process according to claim 4, in which the step 4-a) is performed with an ionic exchange column.

18. The process according to claim 5, in which the step 4-a) is performed with an ionic exchange column.

19. The process according to claim 6, in which the step 4-a) is performed with an ionic exchange column.

20. The process according to claim 7, in which the step 4-a) is performed with an ionic exchange column.

* * * * *